United States Patent
Yen et al.

(10) Patent No.: US 9,211,089 B2
(45) Date of Patent: Dec. 15, 2015

(54) OPTICAL BLOOD GLUCOSE DETECTING APPARATUS AND OPERATING METHOD THEREOF

(75) Inventors: Meng-Shin Yen, Taipei (TW); William Wang, Taoyuan (TW); Chung-Cheng Chou, Taoyuan County (TW); Chung-Ping Chuang, Taoyuan (TW)

(73) Assignee: Crystalvue Medical Corporation, Gueishan, Taoyuan (TW)

( * ) Notice: Subject to any disclaimer, the term of this patent is extended or adjusted under 35 U.S.C. 154(b) by 128 days.

(21) Appl. No.: 13/421,290

(22) Filed: Mar. 15, 2012

(65) Prior Publication Data

US 2012/0238843 A1    Sep. 20, 2012

(30) Foreign Application Priority Data

Mar. 15, 2011    (TW) .............................. 100108761 A

(51) Int. Cl.
  *A61B 5/1455*    (2006.01)
  *A61B 5/145*    (2006.01)

(52) U.S. Cl.
  CPC ........... *A61B 5/1455* (2013.01); *A61B 5/14532* (2013.01)

(58) Field of Classification Search
  CPC .. A61B 5/1455; A61B 5/14532; A61B 5/145; A61B 5/14551; A61B 5/0059; A61B 5/0062; A61B 5/0064; A61B 5/0086

USPC ......... 600/310, 316, 322, 331, 344, 473, 476, 600/333
See application file for complete search history.

(56) References Cited

U.S. PATENT DOCUMENTS

| | | | |
|---|---|---|---|
| 5,139,023 A * | 8/1992 | Stanley et al. | 600/368 |
| 6,180,416 B1 * | 1/2001 | Kurnik et al. | 600/316 |
| 7,389,131 B2 * | 6/2008 | Kanayama | 600/322 |
| 2003/0023151 A1 * | 1/2003 | Khalil et al. | 600/316 |
| 2005/0010090 A1 * | 1/2005 | Acosta et al. | 600/316 |
| 2006/0116563 A1 * | 6/2006 | Asano et al. | 600/319 |

* cited by examiner

*Primary Examiner* — Tse Chen
*Assistant Examiner* — Chu Chuan (JJ) Liu
(74) *Attorney, Agent, or Firm* — Muncy, Geissler, Olds & Lowe, P.C.

(57) ABSTRACT

An optical blood glucose detecting apparatus and an operating method thereof are disclosed. The optical blood glucose detecting apparatus includes a detecting module, an assisting and strengthening module, and a data processing module. The detecting module provides an incident optical signal passing through a detected portion of skin surface into a skin interstitial fluid, captures a blood glucose optical reflection message of the skin interstitial fluid, and it interferes the blood glucose optical reflection message and the incident optical signal to generate a detected data. The assisting and strengthening module provides a physical or chemical effect on a tissue region under the detected portion to strengthen the blood glucose optical reflection message. The data processing module processes the detected data to determine a blood glucose concentration.

2 Claims, 5 Drawing Sheets

OPTICAL BLOOD GLUCOSE DETECTING APPARATUS AND OPERATING METHOD THEREOF

BACKGROUND OF THE INVENTION

1. Field of the Invention

The invention relates to blood glucose detection; in particular, to a non-invasive optical blood glucose detecting apparatus and operating method thereof capable of shortening the light penetrating path to enhance the received optical signal and reduce the noise.

2. Description of the Prior Art

Because most early diabetics have no obvious symptom, if it is caught and suitably treated early, not only serious complications such as heart diseases, stroke, renal failure, blindness, or amputation can be reduced, but also the enormous amount of medical expenses can be saved. Therefore, it is important to continuously detect and control the patient's blood glucose concentration.

In general, the popular blood glucose detection technologies in the market can be divided into two regions: one region is a large blood glucose detecting equipment used in large teaching centers, regional hospitals, or small and medium-sized personal clinics; the other region is a portable blood glucose detecting apparatus. The former mostly cooperates with the medical blood stroke procedure to use the centrifuge, enzymes adding unit, and spectrum analyzer to treat the sample, and the entire blood glucose detection process is very time-consuming. The latter mostly uses invasive blood glucose detection technologies (e.g., the micro invasive blood glucose detection apparatus) to stab the finger tip or other positions of the patient via a blood collection unit to obtain a small amount of blood on the test strips. And then, the test strips will be put in the portable blood glucose detecting apparatus based on the instruction to smoothly read the patient's blood glucose concentration.

For the patient, although the micro invasive blood glucose detection apparatus is more suitable to monitor the patient's blood glucose concentration at home, and the cost and time wasted to and fro the hospital can be saved. However, every time when the patient performs blood glucose detection, he/she has to endure pain from the stabbed finger tip. In case the blood collection unit is not clean enough or repeatedly used, it will be hazardous to the health of the patient, and the collected blood sample may be also polluted, so that the final blood glucose detection result will be inaccurate.

In order to improve the above-mentioned drawbacks of the conventional invasive blood glucose detecting method, the non-invasive blood glucose detecting apparatus has been developed. Please refer to FIG. 1. FIG. 1 illustrates a schematic diagram of the conventional non-invasive blood glucose detecting apparatus. As shown in FIG. 1, the non-invasive blood glucose detecting apparatus 1 performs detection procedure by emitting incident light L to penetrate through the skin surface SK, the skin tissue interstitial fluid GL, and the underlying skin tissue SG, and receiving the reflected optical signal R. Its largest drawback is that the incident light L emitted by the blood glucose detecting apparatus 1 has too long detection path to penetrate through too many layers, so that the optical signal will be gradually attenuated and noise will be also increased. Finally, the strength of the reflected optical signal R received by the blood glucose detecting apparatus 1 is very weak and its signal-to-noise ratio is very small, and the accuracy of the blood glucose concentration detected by the blood glucose detecting apparatus 1 will be largely affected.

Therefore, the invention provides a non-invasive optical blood glucose detecting apparatus and operating method thereof capable of shortening the light penetrating path to enhance the received optical signal and reduce the noise to solve the above-mentioned problems occurred in the prior arts.

SUMMARY OF THE INVENTION

An embodiment of the invention is an optical blood glucose detecting apparatus. In this embodiment, the optical blood glucose detecting apparatus includes a detecting module, an assisting and strengthening module, and a data processing module. The detecting module is used for providing an incident optical signal to pass through a detected portion of a skin surface into a skin interstitial fluid, capturing a blood glucose optical reflection message of the skin interstitial fluid, and interfering the blood glucose optical reflection message and the incident optical signal to generate a detected data. The assisting and strengthening module is used for providing a physical effect or a chemical effect on a tissue region under the detected portion to strengthen the blood glucose optical reflection message. The data processing module is used for processing the detected data to determine a blood glucose concentration.

In practical applications, the physical effect provided by the assisting and strengthening module is generated by a mechanical mechanism, an electronic mechanism, an optical mechanism, a magnetic mechanism, or a sound mechanism. The chemical effect provided by the assisting and strengthening module is generated by a chemical reaction mechanism, a spreading mechanism, or a spraying mechanism.

After the assisting and strengthening module provides the physical effect or the chemical effect on the tissue region to adjust the physical and chemical properties of the tissue region, the data processing module can compare different blood glucose optical reflection messages before and after being assisted and strengthened, or times of assisting and strengthening processes needed to achieve a specific blood glucose concentration to determine a blood glucose concentration.

In addition, the optical blood glucose detecting apparatus can further include a blood glucose concentration database. The blood glucose concentration database is used for storing a plurality of default blood glucose concentrations which are assisted and strengthened, the data processing module compares the blood glucose concentration after being assisted and strengthened with the plurality of default blood glucose concentrations in the blood glucose concentration database to determine whether the detected portion is properly selected.

Another embodiment of the invention is a method of operating an optical blood glucose detecting apparatus. The optical blood glucose detecting apparatus includes a detecting module, an assisting and strengthening module, and a data processing module. The method includes steps of: (a) the detecting module providing an incident optical signal to pass through a detected portion of a skin surface into a skin interstitial fluid, and capturing a blood glucose optical reflection message of the skin interstitial fluid, and interfering the blood glucose optical reflection message and the incident optical signal to generate a detected data; (b) the assisting and strengthening module providing a physical effect or a chemical effect on a tissue region under the detected portion to strengthen the blood glucose optical reflection message; (c) the data processing module processing the detected data to determine a blood glucose concentration.

Compared to the prior arts, the optical blood glucose detecting apparatus of the invention is optical reflection type, and the optical reflection signal captured by optical blood glucose detecting apparatus will be interfered with the reference signal and then processed by the following data processing procedures. Because its detected tissue region is the skin tissue interstitial fluid, and the underlying skin tissue is not necessary to be penetrated, the length of the optical penetrating path can be largely shortened to improve the drawbacks of signal attenuation and noise increasing caused by the long optical penetrating path in prior art.

In addition, the optical blood glucose detecting apparatus of the invention also includes the assisting and strengthening module used to provide the physical effect or the chemical effect on the detected tissue region to adjust the physical and chemical properties of the tissue region to strengthen the blood glucose optical reflection message. The optical blood glucose detecting apparatus of the invention also has the following advantages.

(a) Since the detected tissue region is already assisted and strengthened by the optical blood glucose detecting apparatus, the blood glucose detecting result in the tissue region can be optimized to increase the detection accuracy of the optical blood glucose detecting apparatus.

(b) The optical blood glucose detecting apparatus can compare a plurality of blood glucose detecting results to remove the effect of the noise to the blood glucose concentration to increase the detection accuracy of the optical blood glucose detecting apparatus.

(c) The optical blood glucose detecting apparatus can also build a blood glucose concentration database in advance and determine whether the detected region is suitably selected by comparing data.

(d) The optical blood glucose detecting apparatus can not only use every single data, but also compare different blood glucose optical reflection messages before and after being assisted and strengthened, or times of assisting and strengthening processes needed to achieve a specific blood glucose concentration to determine blood glucose concentration.

The advantage and spirit of the invention may be understood by the following detailed descriptions together with the appended drawings.

BRIEF DESCRIPTION OF THE APPENDED DRAWINGS

DETAILED DESCRIPTION OF THE INVENTION

The invention provides an optical blood glucose detecting apparatus and operating method thereof. The optical blood glucose detecting apparatus of the invention is optical reflection type, and the optical reflection signal captured by optical blood glucose detecting apparatus will be interfered with the reference signal and then processed by the following data processing procedures to determine the blood glucose concentration in the tissue region to be detected. Because its detected tissue region is the skin tissue interstitial fluid, and the underlying skin tissue is not necessary to be penetrated, the length of the optical penetrating path can be largely shortened to improve the drawbacks of signal attenuation and noise increasing caused by the long optical penetrating path in prior art.

Figure 2:
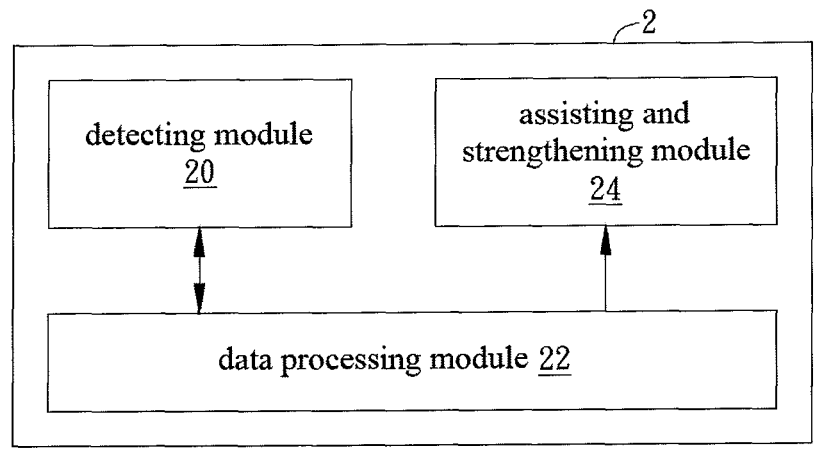
FIG. 2 illustrates a function block diagram of the optical blood glucose detecting apparatus in the first embodiment of the invention.

A first embodiment of the invention is an optical blood glucose detecting apparatus. Please refer FIG. 2. FIG. 2 illustrates a function block diagram of the optical blood glucose detecting apparatus in this embodiment. As shown in FIG. 2, the optical blood glucose detecting apparatus 2 includes a detecting module 20, a data processing module 22, and an assisting and strengthening module 24. Wherein, the data processing module 22 is coupled to the detecting module 20 and the assisting and strengthening module 24.

Next, the modules of the optical blood glucose detecting apparatus 2 and their functions will be introduced in detail as follows.

Before performing blood glucose concentration detection, the detecting module 20 of the optical blood glucose detecting apparatus 2 will select a detected portion of a skin surface at first. In fact, some characteristic points on the skin surface can be used by the detecting module 20 to select the detected portion. For example, the lines on the skin surface can be used as the characteristic points, but not limited to this. In addition, the optical blood glucose detecting apparatus 2 can also store the characteristic points used for positioning and comparison through an image capturing method or other methods, so that the optical blood glucose detecting apparatus 2 can continuously fixed-point detection and tracking in the future.

Figure 3:
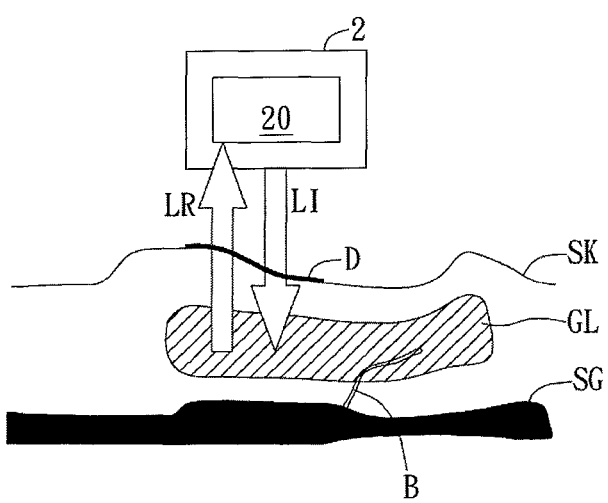
FIG. 3 illustrates a schematic diagram of the optical blood glucose detecting apparatus performing detection.

Afterward, as shown in FIG. 3, because the detected portion D of the skin surface SK has been selected, the detecting module 20 will emit an incident optical signal LI (e.g., the laser with suitable wavelength, but not limited to this) to penetrate through the detected portion D of the skin surface SK, and then emitted toward an underlying skin interstitial fluid GL. The skin interstitial fluid GL is a transparent liquid, and the nutrients (e.g., glucose) can be transmitted to the cells through the skin interstitial fluid GL. When the incident optical signal LI is emitted to the skin interstitial fluid GL, the skin interstitial fluid GL will reflect the incident optical signal LI to form a reflected optical signal LR. When the detecting module 20 receives the reflected optical signal LR, the detecting module 20 can capture a blood glucose concentration optical reflection message BR related to the skin interstitial fluid GL from the reflected optical signal LR.

Figure 1:
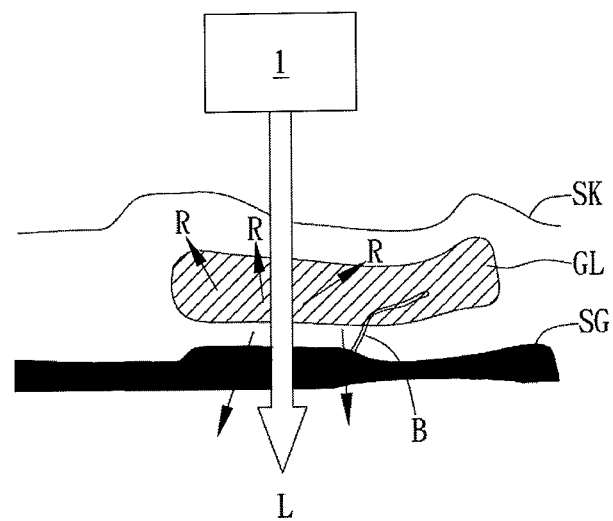
FIG. 1 illustrates a schematic diagram of the conventional non-invasive blood glucose detecting apparatus performing detection.

It should be noticed that as shown in FIG. 1, in the prior art, because the incident light should penetrate through the skin surface SK, the skin interstitial fluid GL, and the underlying skin tissue SG, the optical penetrating path will be too long, and the strength of the received reflected optical signal R will be weak and its signal-to-noise ratio will be also small. On the contrary, since the incident optical signal LI in FIG. 3 of the invention will only penetrate through the detected portion D of the skin surface SK, and then emitted toward the underlying skin interstitial fluid GL without being emitted to the underlying skin tissue SG, the optical penetrating path in the invention is obviously shorter than that in prior art, and the drawbacks of weaker reflected optical signal and smaller signal-to-noise ratio in prior art can be effectively improved to increase the accuracy of the blood glucose concentration detection performed by the optical blood glucose detecting apparatus 2.

After the detecting module 20 captures the blood glucose concentration optical reflection message BR related to the skin interstitial fluid GL from the reflected optical signal LR, the detecting module 20 will interfere the blood glucose concentration optical reflection message BR and a reference signal to generate a first detected data. Then, the detecting module 20 will transmit the first detected data to the data processing module 22, and the data processing module 22 will perform following data processing process to the first detected data to determine the first detected data. That is to say, in fact, the first detected data determined by the data processing module 22 is not under the assisting and strengthening treatment performed on the detected tissue region by the assisting and strengthening module 24.

Then, in order to detect the blood glucose concentration more accurately, the optical blood glucose detecting apparatus 2 will use the assisting and strengthening module 24 to provides a physical effect or a chemical effect on the tissue region under the detected portion to adjust the physical and chemical properties of the tissue region to strengthen the blood glucose optical reflection message. In practical applications, the physical effect provided by the assisting and strengthening module 24 can be generated by a mechanical mechanism, an electronic mechanism, an optical mechanism, a magnetic mechanism, or a sound mechanism, and the chemical effect provided by the assisting and strengthening module 24 can be generated by a chemical reaction mechanism, a spreading mechanism, or a spraying mechanism, but not limited to this.

Figure 4A:
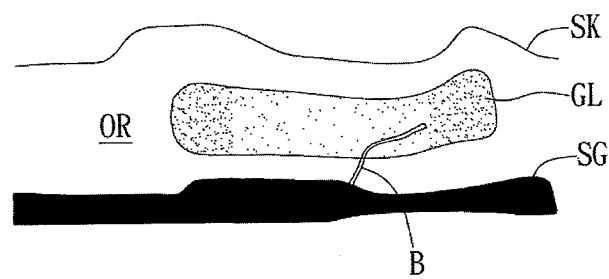
FIG. 4A and FIG. 4B illustrate an embodiment of providing physical effect on the tissue region under the detected portion.
Figure 4B:
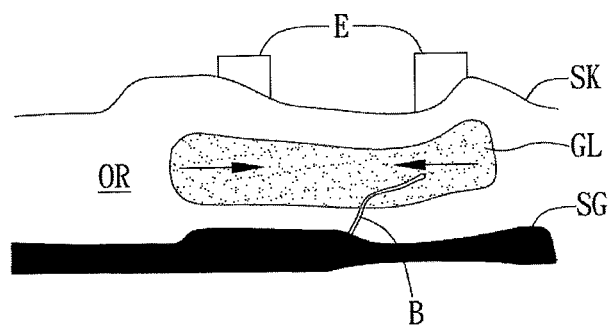

For example, FIG. 4A and FIG. 4B illustrate an embodiment of providing physical effect on the tissue region OR. This embodiment uses the reverse ion electro osmosis method to adjust the distribution of the blood glucose concentration in the skin interstitial fluid GL, so that the blood glucose optical reflection message can be strengthened. In the reverse ion electro osmosis method, when the energy of the low current provided by the electrode E passes through the skin, the salt of the skin interstitial fluid GL under the skin will be taken out, and when the chloride ion and the sodium ion in the salt move to the electrode E, water and glucose will be taken out, so that the uneven distribution of the blood glucose concentration in the skin interstitial fluid GL shown in FIG. 4A will be changed to the uniform distribution of the blood glucose concentration in the skin interstitial fluid GL shown in FIG. 4B.

Figure 4C:
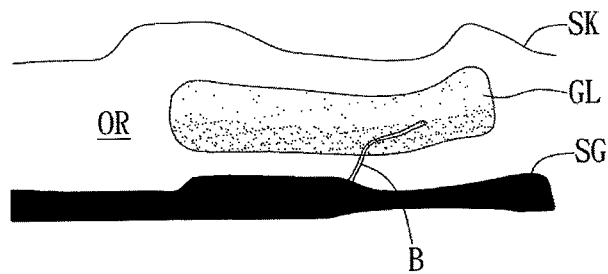
FIG. 4C and FIG. 4D illustrate an embodiment of providing chemical effect on the tissue region under the detected portion.
Figure 4D:
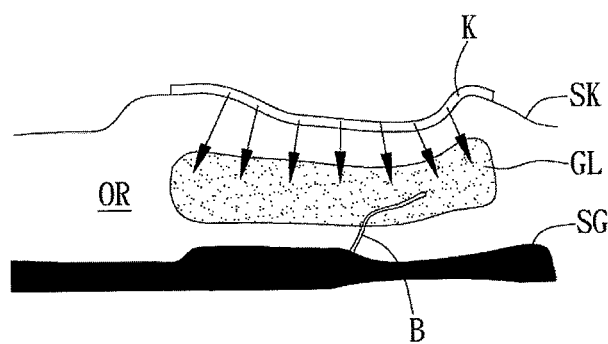

FIG. 4C and FIG. 4D illustrate an embodiment of providing chemical effect on the tissue region OR. This embodiment uses the spreading mechanism to adjust the distribution of the blood glucose concentration in the skin interstitial fluid GL, so that the blood glucose optical reflection message can be strengthened. When the chemicals K spread on the skin penetrate into the tissue region OR under the skin, the chemicals K will generate chemical effect in the skin interstitial fluid GL, so that the uneven distribution of the blood glucose concentration in the skin interstitial fluid GL shown in FIG. 4C will be changed to the uniform distribution of the blood glucose concentration in the skin interstitial fluid GL shown in FIG. 4D.

It should be noticed that the assisting and strengthening module 24 can generate different physical effects or chemical effects on the skin interstitial fluid GL in the tissue region OR based on practical needs to adjust the distribution of the blood glucose concentration in the skin interstitial fluid GL to strengthen the blood glucose optical reflection message and optimize the blood glucose detecting result. It is not limited to the above-mentioned cases. That is to say, the assisting and strengthening module 24 can also adjust the blood glucose concentration in the skin interstitial fluid GL to be the distribution of local high blood glucose concentration based on practical needs, as long as the effect of strengthening the blood glucose optical reflection message can be achieved.

After the assisting and strengthening module 24 finishes the assisting and strengthening treatment to the tissue region under the detected portion D, the detecting module 20 will perform the detecting procedure shown in FIG. 3 again. The detecting module 20 will interfere the captured blood glucose optical reflection message and the reference signal to generate a second detected data. Then, the detecting module 20 will transmit the second detected data to the data processing module 22, and the data processing module 22 will perform following data processing procedure to the second detected data to determine a second blood glucose concentration data. Since the second blood glucose concentration data determined by the data processing module 22 is practically assisted and strengthened by the assisting and strengthening module 24, it is obviously different from the above-mentioned first blood glucose concentration data. After the above-mentioned assisting and strengthening treatment, the optical blood glucose detecting apparatus 2 can optimize its blood glucose detecting result, and the optical blood glucose detecting apparatus 2 can also perform blood glucose detection many times to obtain many blood glucose detecting results to remove the effect caused by the noise.

In practical applications, the optical blood glucose detecting apparatus 2 can not only use every single data (e.g., the above-mentioned first detected data or second detected data) to determine blood glucose concentration, but also compare different blood glucose optical reflection messages before and after being assisted and strengthened, or times of assisting and strengthening processes needed to achieve a specific blood glucose concentration to determine blood glucose concentration. For example, it is assumed that the default times of assisting and strengthening processes needed to achieve the specific blood glucose concentration are 4 times, if the optical blood glucose detecting apparatus 2 has performed the assisting and strengthening treatment over 4 times and still fails to achieve the specific blood glucose concentration, it means that the detected portion selected by the optical blood glucose detecting apparatus 2 is incorrect. Therefore, the optical blood glucose detecting apparatus 2 has to select other detected portions for the following detections.

In addition, the data processing module 22 can include a blood glucose concentration database (not shown in figures). The blood glucose concentration database is used for storing a plurality of default blood glucose concentrations which are already assisted and strengthened, after the data processing module 22 determines the assisted and strengthened second blood glucose concentration data, the data processing module 22 will compare the second blood glucose concentration data with the plurality of default blood glucose concentrations in the blood glucose concentration database to determine whether the detected portion D is properly selected by the detecting module 20. If the determining result of the data processing module 22 is no, it means that the detected portion D selected by the detecting module 20 is incorrect. Therefore, the detecting module 20 has to select other detected portions for the following detections.

Figure 5:
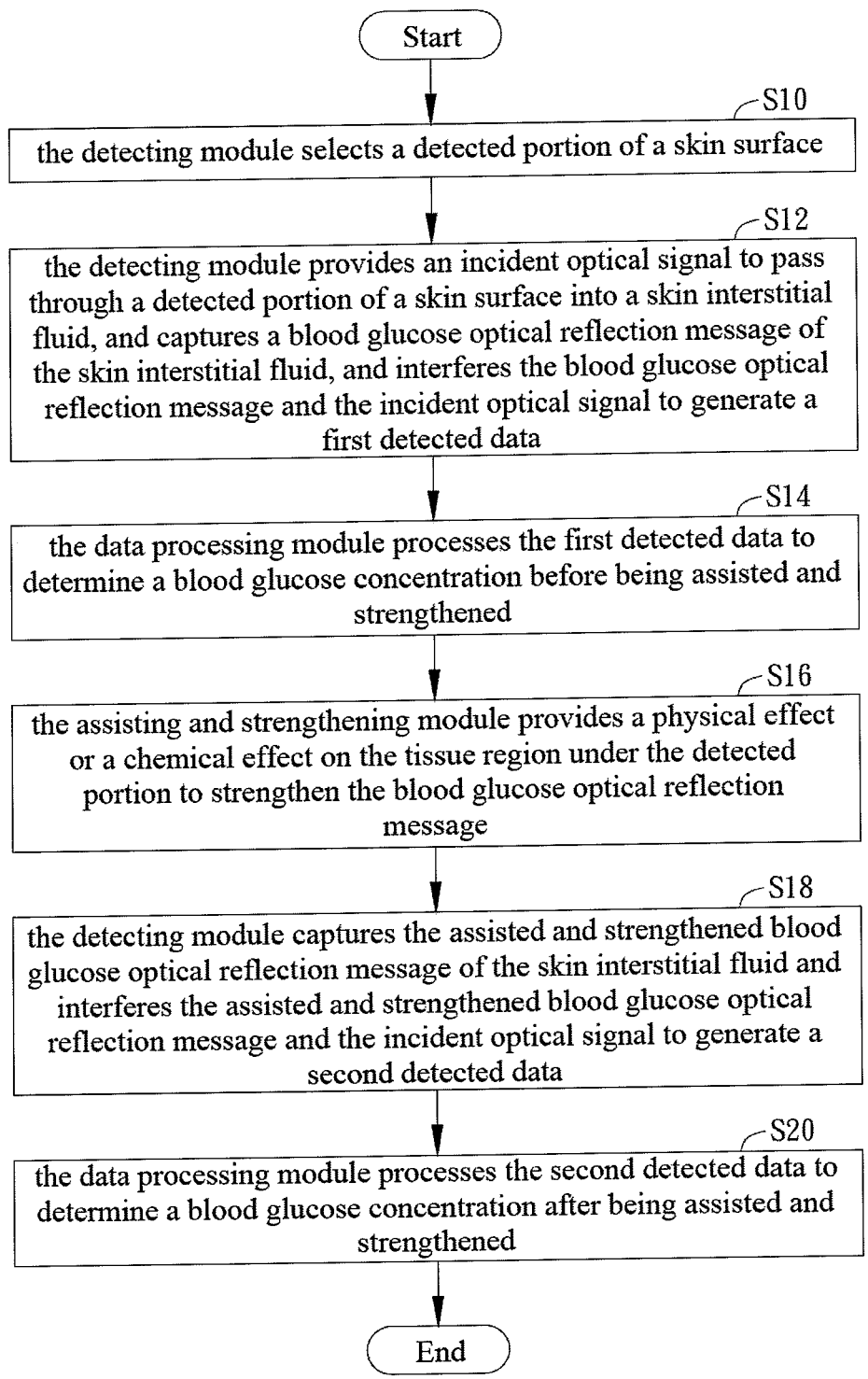
FIG. 5 illustrates a flowchart of the optical blood glucose detecting apparatus operating method in the second embodiment of the invention.

The second embodiment of the invention is a method of operating an optical blood glucose detecting apparatus. In this embodiment, the optical blood glucose detecting apparatus includes a detecting module, an assisting and strengthening module, and a data processing module. Please refer to FIG. 5. FIG. 5 illustrates a flowchart of the optical blood glucose detecting apparatus operating method in the embodiment.

As shown in FIG. 5. At first, the method performs step S10 that the detecting module selects a detected portion of a skin surface. Then, the method performs step S12 that the detecting module provides an incident optical signal to pass through a detected portion of a skin surface into a skin interstitial fluid, and captures a blood glucose optical reflection message of the skin interstitial fluid, and interferes the blood glucose optical reflection message and the incident optical signal to generate a first detected data. Then, the method performs step S14 that the data processing module processes the first detected data to determine a blood glucose concentration before being assisted and strengthened. Then, the method performs step S16 that the assisting and strengthening module provides a physical effect or a chemical effect on the tissue region under the detected portion to strengthen the blood glucose optical reflection message. Afterward, the method performs step S18 that the detecting module captures the assisted and strengthened blood glucose optical reflection message of the skin interstitial fluid and interferes the assisted and strengthened blood glucose optical reflection message and the incident optical signal to generate a second detected data. At last, the method performs step S20 that the data processing module processes the second detected data to determine a blood glucose concentration after being assisted and strengthened.

In fact, the blood glucose concentration data determined by the data processing module in step S20 has been processed by the assisting and strengthening module, therefore, it is obviously different from the blood glucose concentration data determined by the data processing module in step S14 before being assisted and strengthened. After performing the assisting and strengthening treatment of step S16, the method can optimize the blood glucose detecting result and remove the effect caused by the noise by performing detection many times to obtain many detecting results.

In practical applications, the optical blood glucose detecting apparatus can not only use every single data (e.g., the above-mentioned first detected data or second detected data) to determine blood glucose concentration, but also compare different blood glucose optical reflection messages before and after being assisted and strengthened, or times of assisting and strengthening processes needed to achieve a specific blood glucose concentration to determine blood glucose concentration. In step S16, the physical effect provided by the assisting and strengthening module is generated by a mechanical mechanism, an electronic mechanism, an optical mechanism, a magnetic mechanism, or a sound mechanism; the chemical effect provided by the assisting and strengthening module is generated by a chemical reaction mechanism, a spreading mechanism, or a spraying mechanism, but not limited to this.

After the method performs step S16 that the assisting and strengthening module provides the physical effect or the chemical effect on the tissue region to adjust the physical and chemical properties of the tissue region, the data processing module can compare different blood glucose optical reflection messages before and after being assisted and strengthened, or times of assisting and strengthening processes needed to achieve a specific blood glucose concentration to determine a blood glucose concentration.

In addition, the optical blood glucose detecting apparatus can further include a blood glucose concentration database. The blood glucose concentration database is used for storing a plurality of default blood glucose concentrations which are assisted and strengthened, the data processing module compares the blood glucose concentration after being assisted and strengthened with the plurality of default blood glucose concentrations in the blood glucose concentration database to determine whether the detected portion is properly selected in step S10.

Compared to the prior arts, the optical blood glucose detecting apparatus of the invention is optical reflection type, and the optical reflection signal captured by optical blood glucose detecting apparatus will be interfered with the reference signal and then processed by the following data processing procedures. Because its detected tissue region is the skin tissue interstitial fluid, and the underlying skin tissue is not necessary to be penetrated, the length of the optical penetrating path can be largely shortened to improve the drawbacks of signal attenuation and noise increasing caused by the long optical penetrating path in prior art.

In addition, the optical blood glucose detecting apparatus of the invention also includes the assisting and strengthening module used to provide the physical effect or the chemical effect on the detected tissue region to adjust the physical and chemical properties of the tissue region to strengthen the blood glucose optical reflection message. The optical blood glucose detecting apparatus of the invention also has the following advantages.

(a) Since the detected tissue region is already assisted and strengthened by the optical blood glucose detecting apparatus, the blood glucose detecting result in the tissue region can be optimized to increase the detection accuracy of the optical blood glucose detecting apparatus.

(b) The optical blood glucose detecting apparatus can compare a plurality of blood glucose detecting results to remove the effect of the noise to the blood glucose concentration to increase the detection accuracy of the optical blood glucose detecting apparatus.

(c) The optical blood glucose detecting apparatus can also build a blood glucose concentration database in advance and determine whether the detected region is suitably selected by comparing data.

(d) The optical blood glucose detecting apparatus can not only use every single data, but also compare different blood glucose optical reflection messages before and after being assisted and strengthened, or times of assisting and strengthening processes needed to achieve a specific blood glucose concentration to determine blood glucose concentration.

With the example and explanations above, the features and spirits of the invention will be hopefully well described. Those skilled in the art will readily observe that numerous modifications and alterations of the device may be made while retaining the teaching of the invention. Accordingly, the above disclosure should be construed as limited only by the metes and bounds of the appended claims.

What is claimed is:

1. An optical blood glucose detecting apparatus, comprising:
a detecting module, configured to select a detected portion of a skin surface according to characteristic points on the skin surface, provide an incident optical signal to pass through the detected portion of the skin surface into a skin interstitial fluid, capture a blood glucose optical reflection message of the skin interstitial fluid, and interfere the blood glucose optical reflection message and the incident optical signal to generate a detected data, wherein the skin interstitial fluid comprises a chloride ion, a sodium ion, a water, and a glucose, and a blood glucose concentration in the skin interstitial fluid is uneven;

an assisting and strengthening module, comprising:
an electrode, disposed on the detected portion of the skin surface and configured to selectively provide a low current to the skin interstitial fluid under the detected portion of the skin surface to make the chloride ion and the sodium ion in the skin interstitial fluid move toward the electrode, and the water and the glucose being taken out with the chloride ion and the sodium ion to make the blood glucose concentration in the skin interstitial fluid become uniform; and a data processing module, coupled to the detecting module and the assisting and strengthening module and configured to process the detected data according to a plurality of default blood glucose concentrations stored in a blood glucose concentration database to determine a value of the blood glucose concentration and configured to determine whether the detected portion of the skin surface is properly selected by the detecting module or not according to a number of times assisting and strengthening processes are needed to achieve a specific blood glucose concentration, when the number of times of the assisting and strengthening processes needed to achieve the specific blood glucose concentration is larger than a default number of times, the data processing module being configured to determine that the detected portion of the skin surface is not properly selected by the detecting module, and then the detecting module selecting another detected portion for detection;

wherein the blood glucose concentration database is configured to store a plurality of default blood glucose concentrations which are assisted and strengthened, the data processing module is configured to compare the blood glucose concentration after being assisted and strengthened with the plurality of default blood glucose concentrations in the blood glucose concentration database to determine whether the detected portion is properly selected.

2. A method of operating an optical blood glucose detecting apparatus, the optical blood glucose detecting apparatus comprising a detecting module, an assisting and strengthening module, and a data processing module, the assisting and strengthening module comprising an electrode, the method comprising steps of:

(a) the detecting module selecting a detected portion of a skin surface according to characteristic points on the skin surface, providing an incident optical signal to pass through the detected portion of the skin surface into a skin interstitial fluid, capture a blood glucose optical reflection message of the skin interstitial fluid, and interfere the blood glucose optical reflection message and the incident optical signal to generate a detected data, wherein the skin interstitial fluid comprises a chloride ion, a sodium ion, a water, and a glucose, and a blood glucose concentration in the skin interstitial fluid is uneven;

(b) disposing the electrode on the detected portion of the skin surface and the electrode selectively providing a low current to the skin interstitial fluid under the detected portion of the skin surface to make the chloride ion and the sodium ion in the skin interstitial fluid move toward the electrode, and the water and the glucose being taken out with the chloride ion and the sodium ion to make the blood glucose concentration in the skin interstitial fluid become uniform; and (c) the data processing module processing the detected data according to a plurality of default blood glucose concentrations stored in a blood glucose concentration database to determine a value of the blood glucose concentration and determining whether the detected portion of the skin surface is properly selected by the detecting module or not according to a number of times assisting and strengthening processes are needed to achieve a specific blood glucose concentration, when the number of times of the assisting and strengthening processes needed to achieve the specific blood glucose concentration is larger than a default number of times, the data processing module determining that the detected portion of the skin surface is not properly selected by the detecting module, and then the detecting module selecting another detected portion for detection;

wherein the blood glucose concentration database stores a plurality of default blood glucose concentrations which are assisted and strengthened, the data processing module compares the blood glucose concentration after being assisted and strengthened with the plurality of default blood glucose concentrations in the blood glucose concentration database to determine whether the detected portion is properly selected.

* * * * *